(12) United States Patent
Hennings et al.

(10) Patent No.: US 8,439,045 B2
(45) Date of Patent: May 14, 2013

(54) THERMALLY MEDIATED TISSUE MOLDING

(71) Applicants: David R. Hennings, Roseville, CA (US); Michael A. Zaro, Roseville, CA (US); Edward M. Zimmerman, Roseville, CA (US)

(72) Inventors: David R. Hennings, Roseville, CA (US); Michael A. Zaro, Roseville, CA (US); Edward M. Zimmerman, Roseville, CA (US)

(73) Assignee: CoolTouch Incorporated, Roseville, CA (US)

( * ) Notice: Subject to any disclaimer, the term of this patent is extended or adjusted under 35 U.S.C. 154(b) by 0 days.

(21) Appl. No.: 13/631,351

(22) Filed: Sep. 28, 2012

(65) Prior Publication Data

US 2013/0023856 A1   Jan. 24, 2013

Related U.S. Application Data

(60) Division of application No. 12/190,562, filed on Aug. 12, 2008, now Pat. No. 8,276,590, which is a continuation-in-part of application No. 12/101,095, filed on Apr. 10, 2008, now Pat. No. 8,357,146, which is a continuation-in-part of application No. 11/847,153, filed on Aug. 29, 2007, now Pat. No. 8,256,429, which is a continuation-in-part of application No. 11/675,028, filed on Feb. 14, 2007, now Pat. No. 8,127,771, which is a continuation-in-part of application No. 11/131,577, filed on May 18, 2005, now Pat. No. 7,217,265.

(51) Int. Cl.
*A61B 19/00* (2006.01)
*A61N 5/067* (2006.01)

(52) U.S. Cl.
USPC ............... 128/898; 607/89; 607/92; 606/15

(58) Field of Classification Search .......... 606/7, 9, 606/13–16; 607/88–92, 96–102; 128/898
See application file for complete search history.

(56) References Cited

U.S. PATENT DOCUMENTS

| | | |
|---|---|---|
| 4,537,193 A | 8/1985 | Tanner |
| 4,672,969 A | 6/1987 | Dew |
| 4,854,320 A | 8/1989 | Dew |
| 4,868,113 A | 9/1989 | Jaye et al. |
| 4,976,709 A | 12/1990 | Sand |
| 4,985,027 A | 1/1991 | Dressel |
| 5,102,410 A | 4/1992 | Dressel |
| 5,295,955 A | 3/1994 | Rosen et al. |
| 5,304,169 A | 4/1994 | Sand |
| 5,571,216 A | 11/1996 | Anderson |
| 5,618,284 A | 4/1997 | Sand |
| 5,820,626 A | 10/1998 | Baumgardner |

(Continued)

OTHER PUBLICATIONS

U.S. Appl. No. 10/391,221, filed Mar. 17, 2003, by Anderson et al.

(Continued)

*Primary Examiner* — Ahmed Farah
(74) *Attorney, Agent, or Firm* — Ray K. Shahani, Esq.; Kin Hung Lai

(57) ABSTRACT

A method and device to modify tissue in a manner such that it will take on a permanent new shape. Subdermal tissue is heated to approx 60° C. at which point it becomes pliable and moldable and will take on a permanent new shape if allowed to cool and heal in a new position.

8 Claims, 10 Drawing Sheets

U.S. PATENT DOCUMENTS

| | | | |
|---|---|---|---|
| 5,885,274 | A | 3/1999 | Fullmer et al. |
| 5,954,710 | A | 9/1999 | Paolini et al. |
| 5,968,034 | A | 10/1999 | Fullmer et al. |
| 5,976,123 | A | 11/1999 | Baumgardner et al. |
| 6,206,873 | B1 | 3/2001 | Paolini et al. |
| 6,394,973 | B1 | 5/2002 | Cucin |
| 6,398,777 | B1 | 6/2002 | Navarro et al. |
| 6,413,253 | B1 | 7/2002 | Koop et al. |
| 6,419,672 | B1 | 7/2002 | Utsugi |
| 6,443,914 | B1 | 9/2002 | Costantino |
| 6,451,007 | B1 | 9/2002 | Koop et al. |
| 6,470,216 | B1 | 10/2002 | Knowlton |
| 6,589,235 | B2 | 7/2003 | Wong et al. |
| 6,605,080 | B1 | 8/2003 | Altshuler et al. |
| 6,673,096 | B2 | 1/2004 | Lach |
| 6,920,883 | B2 | 7/2005 | Bessette et al. |
| 7,217,265 | B2 | 5/2007 | Hennings et al. |
| 7,713,266 | B2 | 5/2010 | Elkins et al. |
| 8,276,590 | B2 * | 10/2012 | Hennings et al. ............. 128/898 |
| 2004/0116913 | A1 * | 6/2004 | Pilcher et al. .................... 606/9 |
| 2005/0049543 | A1 | 3/2005 | Anderson et al. |
| 2007/0293849 | A1 | 12/2007 | Hennings et al. |
| 2008/0262482 | A1 | 10/2008 | Hantash et al. |

OTHER PUBLICATIONS

U.S. Appl. No. 10/697,212, filed Oct. 30, 2003, by Hennings et al.
U.S. Appl. No. 10/351,273, filed Jan. 24, 2003, by Baumgardner et al.
U.S. Appl. No. 09/934,356, filed Aug. 21, 2001, by Koop.
U.S. Appl. No. 09/134,776, filed Aug. 1998 by Koop et al.
U.S. Appl. No. 10/738,384, filed Dec. 2003 by Hennings et al.
U.S. Appl. No. 11/131,577, filed May 2005 by Hennings et al.
U.S. Appl. No. 09/185,490, filed Jul. 2000 by Koop et al.
U.S. Appl. No. 09/135,330, filed Jul. 1998 by Koop et al.
U.S. Appl. No. 10/160,579, filed May 2002 by Koop et al.
U.S. Appl. No. 10/031,154, filed Jan. 2005 by Koop et al.
U.S. Appl. No. 08/482,208, filed Jun. 1995 by Hennings et al.
U.S. Appl. No. 08/631,800, filed Apr. 1996 by Hennings et al.
U.S. Appl. No. 10/699,212, filed Oct. 2003 by Hennings et al.
U.S. Appl. No. 10/351,273, filed Jan. 2003 by Hennings et al.; and.
U.S. Appl. No. 10/335,176, filed Dec. 2002 by Baumgardner et al.
Dr. Michael Olding, "Does Lipo-dissove Work?" published Jun. 28, 2007, www.washingtonpost.com, 7 pages.
Elisa M. Chavez, "In Vitro Study of Photothermal Laser Effects on Bovine Oral Soft Tissue", ISLD 1992, 4 pages.
U.S. Appl. No. 11/612,324, filed Dec. 2006 by Hennings et al.
Wong et al; "Thermo-Optical response of cartilage during feedback controlled laser-assisted reshaping." SPIE vol. 2975, pp. 310-315. (1997).
Chao et al;"Viability of Porcine Nasal Septal Grafts Following Nd:YAG (?=1.32um) Laser Radiation", SPIE vol. 3914, 543-552 (2000).
Bass et al; "Laser Tissue Welding: A comprehensive reveiw of current and future clinical applications." Lasers in Surgery and Medicine 17:315-349 (1995).
Poppas et al, "Temperature controlled laser photocoagulation of soft tissue: In vivo evaluation using a tissue welding model" Lasers in Surgery and Medicine 18:335-344 (1996).
Cilesiz et al:"Controlled temperature tissue fusion: Argon laser welding of canine intestine in vitro." Lasers in Surgery and Medicine 18: 325-344 (1996).
U.S. Appl. No. 11/101,095, filed Apr. 10, 2008 by Hennings et al.

\* cited by examiner

US 8,439,045 B2

THERMALLY MEDIATED TISSUE MOLDING

RELATED APPLICATIONS

This application is a Divisional of related U.S. patent application Ser. No. 12/190,562 filed Aug. 12, 2008 entitled TREATMENT OF CELLULITE AND ADIPOSE TISSUE WITH MID-INFRARED RADIATION, now U.S. Pat. No. 8,276,590, soon to be issued on Oct. 2, 2012, which is a Continuation-In-Part of related U.S. patent application Ser. No. 12/101,095 filed Apr. 10, 2008 entitled TREATMENT OF CELLULITE AND ADIPOSE TISSUE WITH MID-INFRARED RADIATION, which is a Continuation-In-Part of related U.S. patent application Ser. No. 11/847,153 filed Aug. 29, 2007 entitled TREATMENT OF CELLULITE AND ADIPOSE TISSUE WITH MID-INFRARED RADIATION, now U.S. Pat. No. 8,256,429 issued Sep. 4, 2012, which is a Continuation-In-Part of related U.S. patent application Ser. No. 11/675,028 filed Feb. 14, 2007 entitled TREATMENT OF CELLULITE AND ADIPOSE TISSUE WITH MID-INFRARED RADIATION, now U.S. Pat. No. 8,127,771 issued Mar. 6, 2012, which is a Continuation-In-Part of related U.S. Pat. No. 7,217,265 issued May 15, 2007, application Ser. No. 11/131,577 filed May 18, 2005 entitled TREATMENT OF CELLULITE WITH MID-INFRARED RADIATION, Attorney Docket No. CTI-401, which all are incorporated herein by reference in their entireties, and claims any and all benefits to which they are entitled therefrom.

FIELD OF THE INVENTION

This invention is related to a treatment method and a device of molding tissue, and more specifically to a method and device for thermally altering tissue structure by physical shaping, molding and cooling in order to attain a permanent new shape.

BACKGROUND OF THE INVENTION

Prior art that teaches and describes related methods and/or devices include but are not limited to the following:

U.S. Pat. Nos. 5,618,284 and 4,537,193 to Sand entitled "Collagen shrinkage";

U.S. Pat. Nos. 4,854,320 and 4,672,969 to Dew entitled "Tissue welding";

U.S. Pat. No. 6,589,235 to Wong and Sobol entitled "Cartilage shaping";

U.S. Pat. No. 5,571,216 to Anderson entitled "Wound Healing";

U.S. Pat. No. 6,206,873 to Paolini entitled "Laser Lipolysis";

U.S. Pat. Nos. 4,985,027 and 5,102,410 to Dressel entitled "Soft Tissue aspiration";

U.S. Pat. No. 5,295,955 to Rosen entitled "Microwave aided liposuction";

U.S. Pat. No. 6,394,973 to Cucin entitled "Power assisted liposuction";

Wong et al; "Thermo-Optical response of cartilage during feedback controlled laser-assisted reshaping." SPIE vol. 2975, pp. 310-315. (1997);

Chao et al; "Viability of Porcine Nasal Septal Grafts Following Nd:YAG (?=1.32 um) Laser Radiation", SPIE vol 3914, 543-552 (2000);

Bass et al; "Laser Tissue Welding: A comprehensive review of current and future clinical applications." Lasers in Surgery and Medicine 17:315-349 (1995);

Poppas et al: "Temperature controlled laser photocoagulation of soft tissue: In vivo evaluation using a tissue welding model" Lasers in Surgery and Medicine 18:335-344 (1996); and Cilesiz et al: "Controlled temperature tissue fusion: Argon laser welding of canine intestine in vitro." Lasers in Surgery and Medicine 18: 325-344 (1996).

Sand teaches a method of collagen shrinkage. He does not teach deliberate or precise shaping of the collagen nor does he teach that the tissue becomes pliable and can be formed into shapes determined by other mechanisms than the mechanical stresses from shrinkage of the collagen fibrils. He does not teach that the partially denatured collagen can be moved and bonded to other areas of collagen. He does not teach the use of fat cells to change the shape of skin.

Dew teaches the use of the 1320 nm YAG laser to heat collagenous tissue to join severed tissue and close wounds. He only teaches to repair tissue, not to mold and create new shapes. He does not teach the use of fat cells to assist in the shaping. Dew teaches the use of electronically controlled temperature feedback devices but his devices are not percutaneous.

Wong and Sobol teach the heating and shaping of cartilage using laser or RF devices. They do not teach use of material from other tissue areas or use fat to assist in the shaping. Cartilage is not found in dermal tissue.

Anderson teaches to denature only a fraction of each collagen fibril to stimulate re-attachment of a wound. He does not teach moving collagen around or to use fat for shaping.

Paolini teaches to melt fat with a laser. He does not teach the denaturation, cross-linking or remodeling of collagen or the ability to reshape the tissue with intact fat cells.

Dressel teaches to cut fat with a laser suction device and does not describe or relate to collagen or molding.

Rosen and Cucin teach fat removal via heating devices and do not describe or relate to collagen or tissue molding.

Other prior art teaches stimulating the generation of new collagen with a variety of optical, electromagnetic, and cosmetic means. U.S. Pat. No. 6,443,914 issued Sep. 3, 2002 to Constantino teaches the use of ultrasound to build additional fibrous tissue through the normal body repair mechanism.

U.S. Pat. No. 4,985,027 issued Jan. 15, 1991 to Dressel teaches a soft tissue aspiration device and method of use. However, the laser delivery tip of the optical fiber laser device is protected within the distal tip of the cannula, and there is no extension of the firing tip of the optical fiber beyond the distal tip of the cannula. Thus, this patent is limited to a contained tip configuration.

U.S. Pat. No. 6,470,216 issued Oct. 22, 2002 to Knowlton teaches the use of a radio frequency generator to heat and ablate sub-dermal fat and regenerate collagen for skin tightening. RF energy is known to be highly absorbed in fatty tissue.

U.S. Pat. No. 6,673,096 issued Jan. 6, 2004 to Lach teaches the simultaneous delivery of infrared laser radiation in the range of 650 to 1295 nm and massage devices. It is specifically stated that the objective of the invention is to heat deep layers of tissue and cause lipolysis or decomposition of fatty tissue. This range of wavelengths may heat the fatty tissue but not target the connective collagen as in the present invention. In addition, it is not stated that any fluence levels are required and may be trying to perform bio-stimulation with low-level radiation. The present invention clearly requires adequately high fluence levels to shrink or denature collagen and does not require bio-stimulation to be effective.

U.S. Pat. No. 6,605,080 issued Aug. 12, 2003 to Altshuler et al. teaches a method of selectively targeting fatty tissue while avoiding damage to tissue for the purpose of fat removal. The present invention proposes exactly the opposite in order to alter the collagen containing connective tissue, which is the true cause of cellulite and adipose tissue. Altshuler et al. teaches that the optical absorption spectra of fatty tissue is very different from the absorption spectra of surrounding tissue because of the presence of vibrational modes in the molecules of lipids that form fatty tissue. Since both fatty tissue and water based tissue such as collagen can both be found in the same parts of the skin, the difference in these two optical absorption spectra allows a way to selectively target only one of the types of tissue while reducing the heat absorbed by the other; and henceforth preserving it. Altshuler et al. teaches only the ability to heat fat while sparing tissue. Altshuler et al. does not teach that the opposite can be applied under special conditions.

U.S. Pat. No. 5,304,169 issued Apr. 19, 1994 to Sand and U.S. Pat. No. 4,976,709 issued Dec. 11, 1990 to Sand teach that collagen goes through several stages of alteration when heated. At temperatures lower or around 50° C., collagen is not affected. At about 60° C., collagen may contract and shrink by about 30% without denaturization or permanent damage to the structure. It has been shown that at these temperatures the shrinkage is long term and the collagen remains viable. At temperatures greater than about 65° C. however the collagen will denaturize and lose its elasticity and collapse. When this happens to a connective fiber the fiber may weaken, stretch, and possibly break.

U.S. Pat. No. 6,413,253 issued Jul. 2, 2002 to Koop et al., U.S. Pat. No. 6,451,007 issued Sep. 17, 2002 to Koop et al. and U.S. Pat. No. 5,885,274 issued Mar. 23, 1999 to Fullmer et al. teach a mid-IR laser directed to the surface of the skin with energy densities of 10 to 150 J/cm2 and pulse widths of 5 to 500 msec. A pulsed cryogen cooling system is used to protect the epidermis by spraying a burst of R134a cryogen onto the treatment site immediately pre or post laser treatment.

A need exists for a better way to tighten or sculpt skin in plastic surgical procedures. The traditional technique to deal with loose skin is to excise a section of the dermis as in a face-lift or abdominoplasty. This requires a highly skilled surgeon, has risks associated with wound care and anesthesia, and often leaves the patient with a stretched look with thin skin. Non ablative skin tightening techniques that deliver energy through the dermis to shrink or stimulate new collagen are not effective on large areas with a lot of fat or tissue to treat and damage the dermis. Adhesives such as cyanoacrylate (super glue) or fibrin sealants such as Tisseel™ from Baxter Healthcare are used to invasively hold loose skin while it heals in place. These glues are not natural and have many complications.

ADVANTAGES AND SUMMARY OF THE INVENTION

The present invention relies on a combination of selective absorption by collagen in fibrous strands or connective tissue and surface cooling to prevent epidermal damage.

The present invention consists of a percutaneous energy delivery probe inserted beneath the dermis. The energy, preferably generated by a laser with a wavelength that can selectively heat collagen containing tissue, is delivered through a fiber optic probe and heats the underside of the dermis along with fat cell walls and connective tissue in the fat layer. Connective tissue is broken up, fat cells are allowed to freely move, collagen in the lower dermis reaches a partially denatured state and the skin takes on a feeling like warm clay. Disrupted fat cell material can be removed via aspiration to reduce the tissue volume and the remaining intact fat cells can be relocated to act as a filler material. The skin is held in a new desired position where it will stick or mold to the new shape as the collagen fragments cross link and will continue to improve as the body heals and new collagen is generated in the tissue.

This technique can be used to shape loose skin after liposuction or laser lipolysis procedures. It can be used to flatten and smooth the bumps in cellulite. It can be used to improve the appearance of skin after bariatric surgery or weight loss.

One object and advantage of the present invention is that the procedure is minimally invasive and can be performed through one or more small incisions. In general, it does not involve the cutting of muscle or extensive dermal tissue and wound care is greatly reduced along with the risk of infection. It can be done under local tumescent anesthesia instead of general. A solution can be added to the tumescent to increase its dispersion into interstitial space, which increases tissue permeability and facilitates visualization of the natural topography of the treatment area. The tissue to be targeted is directly in front of the energy delivery system so the risk of epidermal damage is reduced. External conformational change can be seen immediately due to the cross linking of partially denatured collagen but there is also continued long term improvement due to the wound healing process of the body in response to the thermal injury of the tissue. New collagen is generated by the body over the next several months which will reinforce the collagen links generated by the procedure.

Lasers in the wavelength region of 1.2 µm to 1.8 µm have been used for many years to shrink and damage collagen for dermatological purposes. Altshuler specifically points out that the result of utilizing a wavelength region of 1.3 µm to 1.6 µm is extremely poor in his fat removal invention because of the poor absorption in fat within the region. Therefore, lasers in the region of 1.3 µm to 1.6 µm are very suitable to be used to selectively shrink or damage collagen in the presence of fatty tissue. The present invention recognizes this fact and combines it in a novel and unique manner with the established good collagen absorption properties of that wavelength region to make a very useful invention. This particular aspect of the present invention accomplishes the opposite of Altshuler.

The selective nature of several bands of infrared electromagnetic radiation allows the collagen to be heated without damage to the surrounding fatty tissue. A combination of selective absorption by collagen in fibrous strands and surface cooling to prevent epidermal damage enables the present invention to work. Strands that are pulling tightly on crevasses in the skin are heated to the point of denaturization, causing them to relax, expand and release the skin outward. On the other hand, strands that connect to outward bulging areas are heated merely to the non-damaging collagen shrinkage temperature of about 60° C. so they permanently contract and help smooth the skin surface.

In particular the Nd:YAG laser, when operated at a wavelength of 1.32 um, is nearly perfect to selectively damage collagen in the presence of fat. Wavelengths longer than 1.6 um will not be able to penetrate deep enough through the epidermal tissue to reach the target depth and wavelengths shorter than 1.3 um do not have enough water absorption to effectively heat the collagen strands. However, when this invention is used in a percutaneous manner utilizing a fiber optic probe, wavelengths such as 2.0 um would be very effective.

The present invention provides a system and method to mold tissue by thermally shrinking cellulite and adipose tissue connective strands while weakening and stretching others. Strands in the valleys of the cellulite and adipose tissue dimples are stretched and weakened while strands near the upper hill, top or surface of the dimple are shrunk to pull the top of the dimple inward. Precise control of the heating temperature is critical to accomplish this simultaneously. Radiation fluence must be high (>1 J/cm2) enough to cause permanent shrinkage or denaturization of the collagen in the connective tissue. Low-level fluence (<1 J/cm2) will not work to break connective tissue bonds, but they may stimulate fatty tissue reduction. The improved method to accomplish this is to vary the pulse length of the laser so it will selectively cut or heat and shrink the appropriate target tissue.

The method of the present invention requires a temperature feedback device such as a thermal sensing handpiece with feedback controls that is in direct contact with treated tissue. The tissue to be molded will be treated at a higher temperature (>70 deg C.) to break the connective strands and will be treated at a lower temperature (50 to 70 deg C.) to shrink the connective strands. Cooling can be used to prevent surface damage to the epidermis and allow repeated passes over the same spot to drive the heat deep. Less cooling and fluence is used to limit penetration and reduce the target temperature. The fatty tissue may be heated enough to start to metabolize faster but the selective nature of energy at a wavelength of 1320 nm passes directly through the fat to target, i.e., be absorbed by, the fibrous strands. Also, the fat is useful to maintain a smooth and healthy appearance of the skin, in contradistinction to the teachings of the prior art.

Heretofore it was not known how to target and damage fibrous strands without causing extensive damage to surrounding tissue. However, by selecting an energy source that matches the transmission bands of fatty tissue and also matches the absorption bands of collagen and simultaneously varies the pulse length of the energy, it is now possible to accomplish this goal.

The pulse width of the laser can be adjusted by the use of IGBT devices in the power supply that are able to modulate the current flow to the flashlamp in the laser cavity. The pulse length of the laser can also be modulated by the use of discrete capacitors and inductors in the pulse forming network of the power supply. The most effective pulse lengths for ablation or cutting are in the microsecond region, and are preferably between about 20 and about 100 microseconds, or more or less. This short pulse is capable of generating sufficient peak energies to generate plasma effects or photoacoustic effects at the fiber tip which have been shown to cut and ablate tissue with minimal coagulative side effects.

Effective pulse lengths for connective tissue shrinking or coagulating are in the millisecond region, preferably between about 0.5 and about 50 milliseconds, or more or less. These long pulses will not generate plasma effects or photoacoustic effects at the fiber tip but will gently heat and shrink collagen in the connective collagen tissue.

The present invention is utilized inserting a fiber optic energy delivery probe into the skin at the location of the fibrous strands and treating them directly. The use of fiber optic delivery systems for laser energy is well known in the industry, but the use of this technique with a selectively absorbing energy source to treat cellulite and adipose tissue is not obvious. Prior attempts to try this have used energy sources that did not distinguish between the collagen and the fat and the result was extensive damage to all the surrounding tissue and a poor cosmetic result. An additional improvement to this percutaneous approach is to use a fiber optic probe that directs the energy out the front or side of the distal end. This allows the probe to be placed along side the connective strands under the skin and cut in a line with the energy pointed away from the skin surface. It is also possible to perform this procedure under ultrasound imaging to more accurately locate and cut the connective strands. The use of energy in the range of 1.3-1.6 μm or 1.9 to 2.2 μm allows the strands to be cut without affecting the surrounding fatty tissue. In this embodiment the use of the more highly absorbing 2.0-3.0 um radiation such as produced by a Thulium, Holmium, or Erbium doped YAG crystal may be more appropriate as the use of a percutaneous fiber optic makes it unnecessary to optically penetrate the epidermis to reach the target tissue.

Lasers that could be used for this invention include Nd:YAG at 1320 nm, Diode lasers at 1450 nm, ER:Glass laser at 1540 nm, fiber lasers at 1550-1600 nm, Holmium or Thulium lasers at 1.9-2.2 um or Erbium lasers at 2.9 um.

It is yet a further object and advantage of the present invention to provide a method for treating cellulite and adipose tissue by moving the end of the optical fiber past the end of a cannula so that heat does not impinge on the needle tip and heat it up. In one embodiment, the smooth and optionally blunt end of the cannula, rather than sharpened piercing tip, prevents inadvertent puncture of skin and is safer overall to use. The apparatus includes a relatively stiff or rigid polyimide coated optical fiber, optionally cleaved flat or at an angle, providing the advantage of not requiring the use of the cannula and resistance by the fiber to breakage particularly during placement or use. By extending the firing tip of the fiber optic past the distal end of the cannula, the firing tip is well beyond the cannula and there is no risk of overheating the cannula. The fiber can also be made of sapphire crystal. This material is strong enough to not break in the tissue and can transmit laser wavelengths in the 3 um band such as the Erbium YAG laser at 2.94 um.

The tip of the fiber can be extended beyond or past the end of the cannula tip so that it is no longer adjacent the cannula tip, increasing maneuverability and improving the efficiency of the cutting tip. Additionally, by moving the distal tip of the optical fiber well past the tip of the cannula there is less chance that the metal cannula will be heated by the laser beam exiting from the emitting face of the fiber, it provides an advantage to minimize heating of the tip of the cannula which if heated may cause burns to the patient's skin as it is introduced and/or withdrawn before, during or after use. Having the fiber in direct contact with treated tissue allows much higher power density and faster ablation. Moreover, the laser energy from the fiber is distributed more uniformly into the target tissue compared to side-firing cannulae. Also, it allows simultaneous effect of fat ablation and heating of tissue to cause collagen contraction or collagen stimulation.

Removing melted fat, tissue and blood during treatment by the integral suction system enables higher laser ablation efficiency.

A thermal sensor inserted in the cannula allows continuous real time thermal feedback at the precise location of treatment. Real time feedback allows more precise thermal monitoring and control of laser intensity to avoid harmful damage to patient. Compared to the non-contact thermal sensor that can only detect skin temperature, the present apparatus and method is more precise and sensitive to variation in skin thickness, density and surrounding temperature.

It is also an object and advantage of the invention to use a Touhy Borst clamp on the fiber as a marker to guarantee that the fiber is well beyond the cannula tip. Using an aiming beam up to 10 times or more brighter than the conventional aiming beam, the practitioner can easily determine exactly where the fiber tip is and be able to move it well past the cannula tip before firing it to ablate the undesirable connective tissue.

Objects and advantages of the present invention, therefore, include but are not limited to the following:

1. The fiber assists in advancing the cannula by cutting through fibrous strands.
2. Suction on the cannula is activated as the cannula is advanced, pushing it into the fat melted by the protruding fiber. Thus, fat will be liquefied prior to entering the cannula then aspirated or suctioned out through the vacuum delivery and waste disposal aspiration tube. Additionally, the heat is delivered to tighten the overlying skin.
3. Melted fat is detected by increased popping sound of the pulsed laser which indicates that it is time to activate suction and remove the excess liquid fat to allow higher laser ablation efficiency.
4. Having the fiber protrude out the end allows the simultaneous effect of fat ablation and of heating tissue to cause collagen contraction or collagen stimulation. This would be impossible with an enclosed fiber.
5. A special plastic bushing at the tip of the cannula will prevent damage to the fiber as it protrudes out the hole in the tip.
6. A polyimide coated fiber can be used in conjunction with a suction cannula with a hole in the end, the advantage being that the hole can be made very small and the fiber will not obstruct the flow of fat suctioned into the cannula.

Thus, the present device and method of use improves the outcome of conventional liposuction in small areas such as the neck, chin and arms and now is fast enough to be effectively used on larger areas such as the abdomen and thighs.

Further objects and advantages of the present invention will become apparent through the following descriptions, and will be included and incorporated herein.

DETAILED DESCRIPTION OF THE EMBODIMENT

Figure 1:
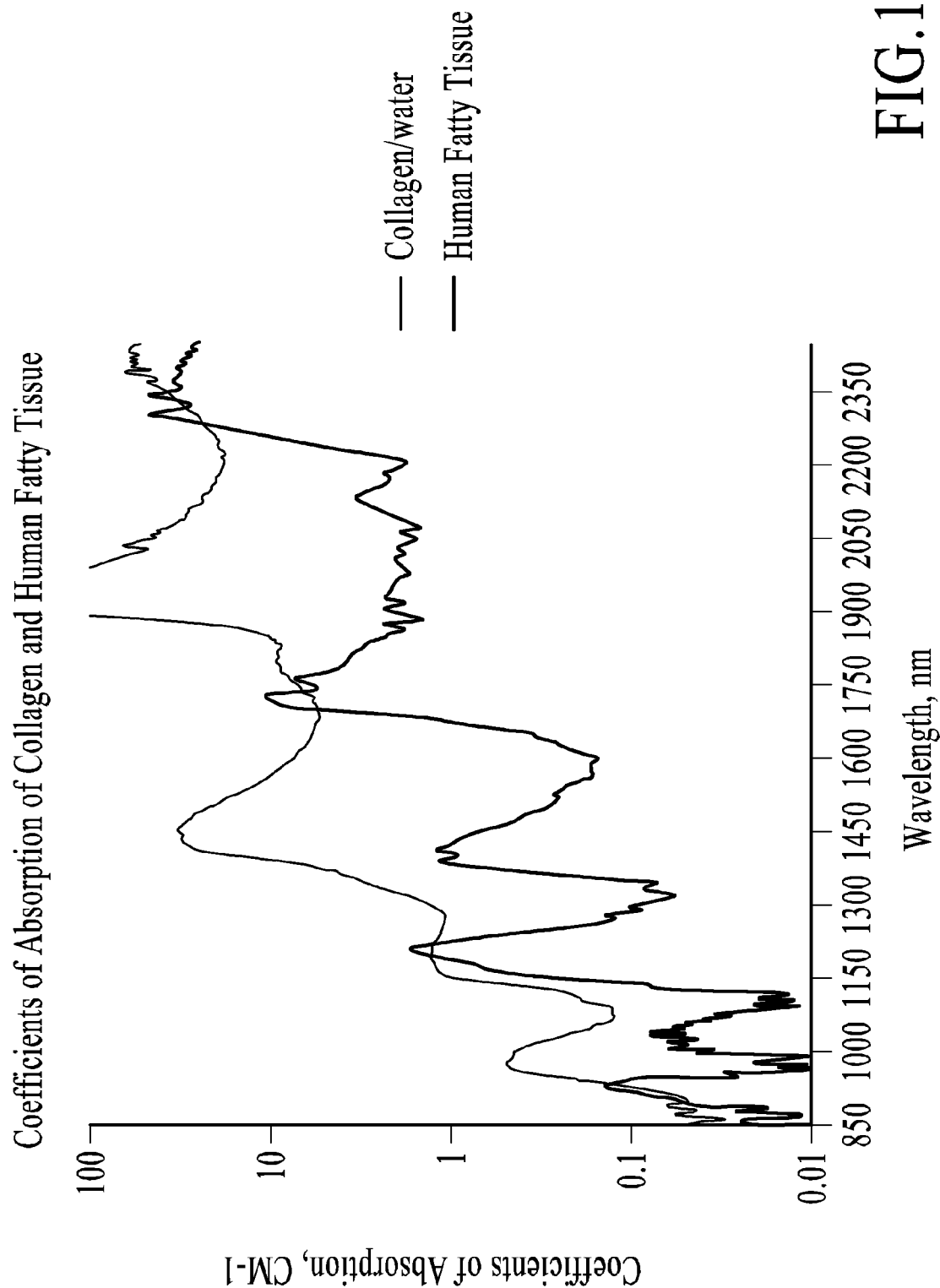
FIG. 1 is a graph illustrating the infrared absorption curves of collagen/water and human fatty tissue 124.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event that component parts of different embodiments have similar structure, functions or uses, they may have been given similar or identical reference numerals and descriptions. It will be understood that such duplication of reference numerals is intended solely for clarity, consistency and ease of understanding the present invention, and are not to be construed as limiting in any way or as implying, for example, that the various embodiments themselves are identical.

Definitions

An "absorption coefficient" of a substance is a measure of the fraction of incident light that is absorbed when light is passed through the substance. The absorption coefficient (typically in units of cm.sup.−1) varies with the nature of the absorbing substance and with the wavelength of the light.

"Collagen" as used herein refers to any of the several types of collagen.

A "wound" as used herein, refers to any damage to any tissue in a living organism. The tissue may be an internal tissue, such as the stomach lining or a bone, or an external tissue, such as the skin. As such, a wound may include, but is not limited to, a gastrointestinal tract ulcer, a broken bone, a neoplasia, and cut or abraded skin. A wound may be in a soft tissue, such as the spleen, or in a hard tissue, such as bone. The wound may have been caused by any agent, including traumatic injury, infection or surgical intervention.

A "growth factor" as used herein, includes any soluble factor that regulates or mediates cell proliferation, cell differentiation, tissue regeneration, cell attraction, wound repair and/or any developmental or proliferative process. The growth factor may be produced by any appropriate means including extraction from natural sources, production through synthetic chemistry, production through the use of recombinant DNA techniques and any other techniques, including virally inactivated, growth factor(s)-rich platelet releasate, which are known to those of skill in the art. The term growth factor is meant to include any precursors, mutants, derivatives, or other forms thereof which possess similar biological activity(ies), or a subset thereof, to those of the growth factor from which it is derived or otherwise related.

FIG. 1 is a graph illustrating the infrared absorption curves of collagen/water and human fatty tissue 124. The graph illustrates the coefficient of absorption (CM-1) of collagen and of human fatty tissue 124 as a function of wavelength respectively. As shown in FIG. 1, the optical absorption spectra of fatty tissue 124 is very different from that of collagen because of the presence of vibrational modes in the molecules of lipids that form fatty tissue 124. The coefficient of absorption of human fatty tissue 124 is extremely low in the wavelength region of 1.3 µm to 1.6 µm indicating poor absorption in fat within the region. The peak coefficient of absorption of fatty tissue 124 absorbing bands are 0.90µ-0.93 µm, 0.119 µm-0.122 µm, and 0.17 µm-0.173 µm. However, as also shown in FIG. 1, the coefficient of absorption of water-based collagen is relatively high in the wavelength region of 1.3 µm to 1.6 µm indicating good infrared absorption. The system 100 of present invention combines this understanding with the established high coefficient of absorption of collagen in that wavelength region. Therefore, lasers having output in the region of between about 1.3 µm and about 1.6 µm and between about 1.9 um and about 2.2 um are very suitable to selectively shrink or denaturize collagen containing connective tissue 122 in the presence of fatty tissue 124.

Figure 2:
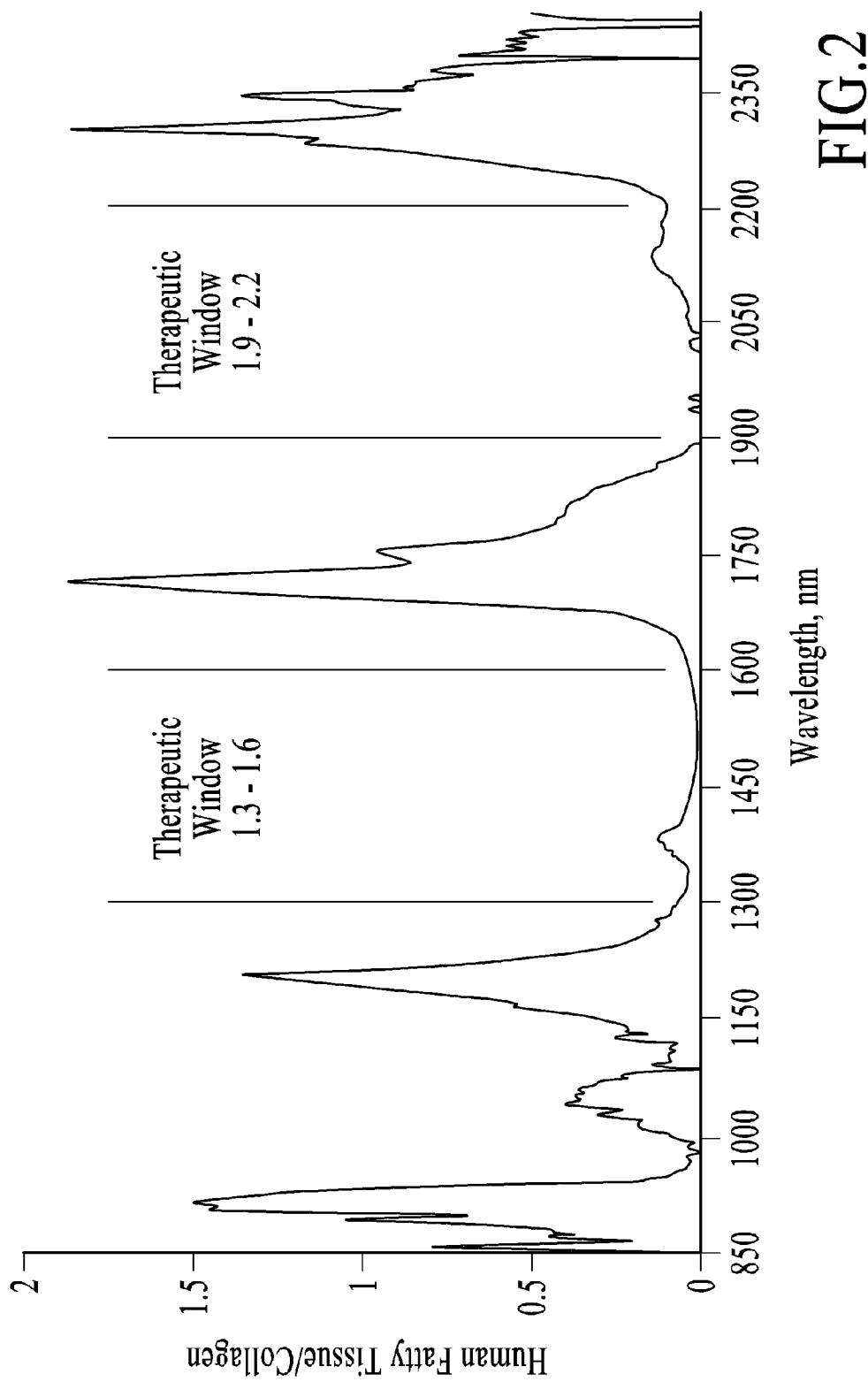
FIG. 2 is a graph illustrating the ratio of the coefficients of infrared absorption of human fatty tissue 124 and collagen as a function of wavelength.

FIG. 2 is a graph illustrating the ratio of the coefficients of infrared absorption of human fatty tissue 124 and collagen as a function of wavelength. As indicated, the higher the ratio, the larger the difference between infrared absorption of fatty tissue 124 and that of collagen; and vice versa. As shown in FIG. 2, there are windows where the ratio between fatty tissue 124 and collagen is the lowest, these are called "therapeutic windows". "Therapeutic windows" indicate the range of wavelengths where collagen containing connective tissue 122 may be effectively targeted with minimal damage to fatty tissue 124. As shown in FIG. 2, these windows occur in the wavelength range of 1.3 µm-1.6 µm and 1.9 µm-2.2 µm respectively. Wavelengths around 3 um are highly absorbed in both fat and tissue and can be used to cut tissue located directly in front of the fiber probe.

Figure 3:
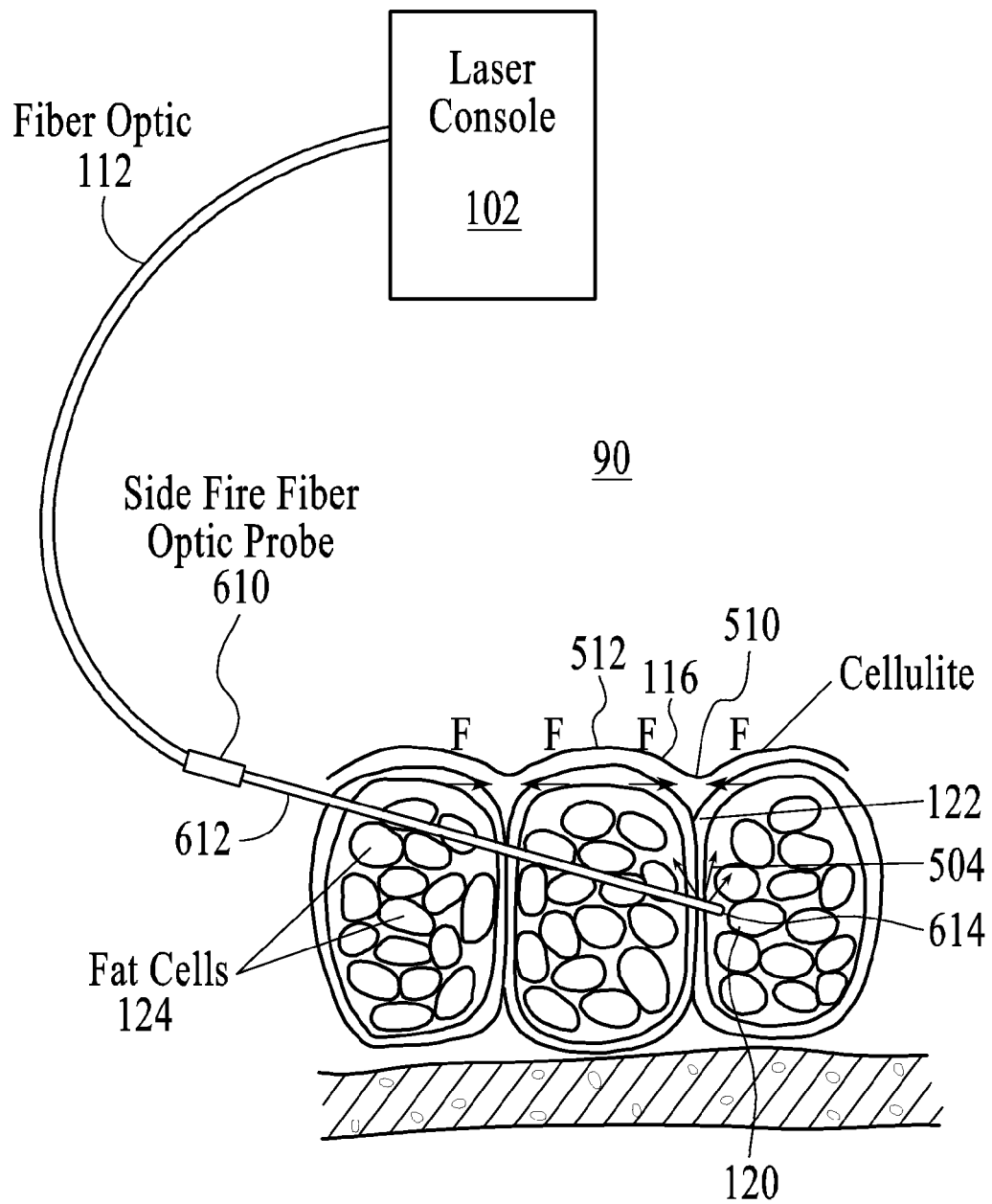
FIG. 3 is a representative detail schematic diagram of an embodiment of the cellulite and adipose tissue treatment system 90 of the present invention.

FIG. 3 is a representative detail schematic diagram of an embodiment of the cellulite and adipose tissue treatment system 90 of the present invention. The system 90 was originally disclosed in related U.S. Pat. No. 7,217,265 to Hennings et. al., which is incorporated herein by reference in their entireties, and claims any and all benefits to which they are entitled therefrom. As shown, the laser energy 110 from the energy source 102 is directed into delivery device 112 which may be a fiber optic, articulated arm, or an electrical cable etc. At the distal end of delivery device 112 is a front or side fire fiber optic probe 610 for directing the laser energy 504 inside the target tissue 120. The front or side fire fiber optic probe 610 includes a long cannula 612 for easy access and a forward or side-firing tip 614 for safe treatment, which may optionally comprise mechanical breaking of the fibers when in contact.

In one embodiment, a fiber optic probe 610 is inserted into the target tissue 120 at the location of the connective fibrous tissue 122. Multiple bursts of laser energy 504, which are from appropriate energy source 102 that matches the transmission bands of fatty tissue 124 and the absorption bands of collagen, are emitted and treat connective fibrous tissue 122 directly. The use of fiber optic delivery systems for laser energy is well known within the industry, but the use of this technique with a selectively absorbing energy source to treat cellulite and adipose tissue is not obvious. Prior attempts to try this have used energy sources that did not distinguish between the collagen and the fat and the result was extensive damage to all the surrounding tissue and a poor cosmetic result. An additional improvement to this percutaneous approach is to use a fiber optic probe 610 that directs the energy out the front or side of the forward or side-firing tip 614. This allows the probe 610 to be placed along side the connective strands 122 under the skin surface 116 and cut in a line with the pulsed energy 504 pointed towards the skin surface 116. In one alternative embodiment, it is also possible to perform this procedure under ultrasound imaging to more accurately locate and treat the connective strands 122, such as those located in the valleys 510 between the dimples of the cellulite and adipose tissue as opposed to those located in the surface tissue 512 of the cellulite tissue. The use of energy in the range of 1.3 µm-1.6 µm or 1.9 µm to 2.2 µm allows the connective tissue 122 to be treated without affecting the surrounding fatty tissue 124. In one embodiment, the use of a more highly absorbing 2.0 µm laser energy 110 such as produced by a Thulium or Holmium doped YAG crystal may be more appropriate as the use of a percutaneous fiber optic makes it unnecessary to optically penetrate the epidermis to reach the target tissue 120.

Figure 4:
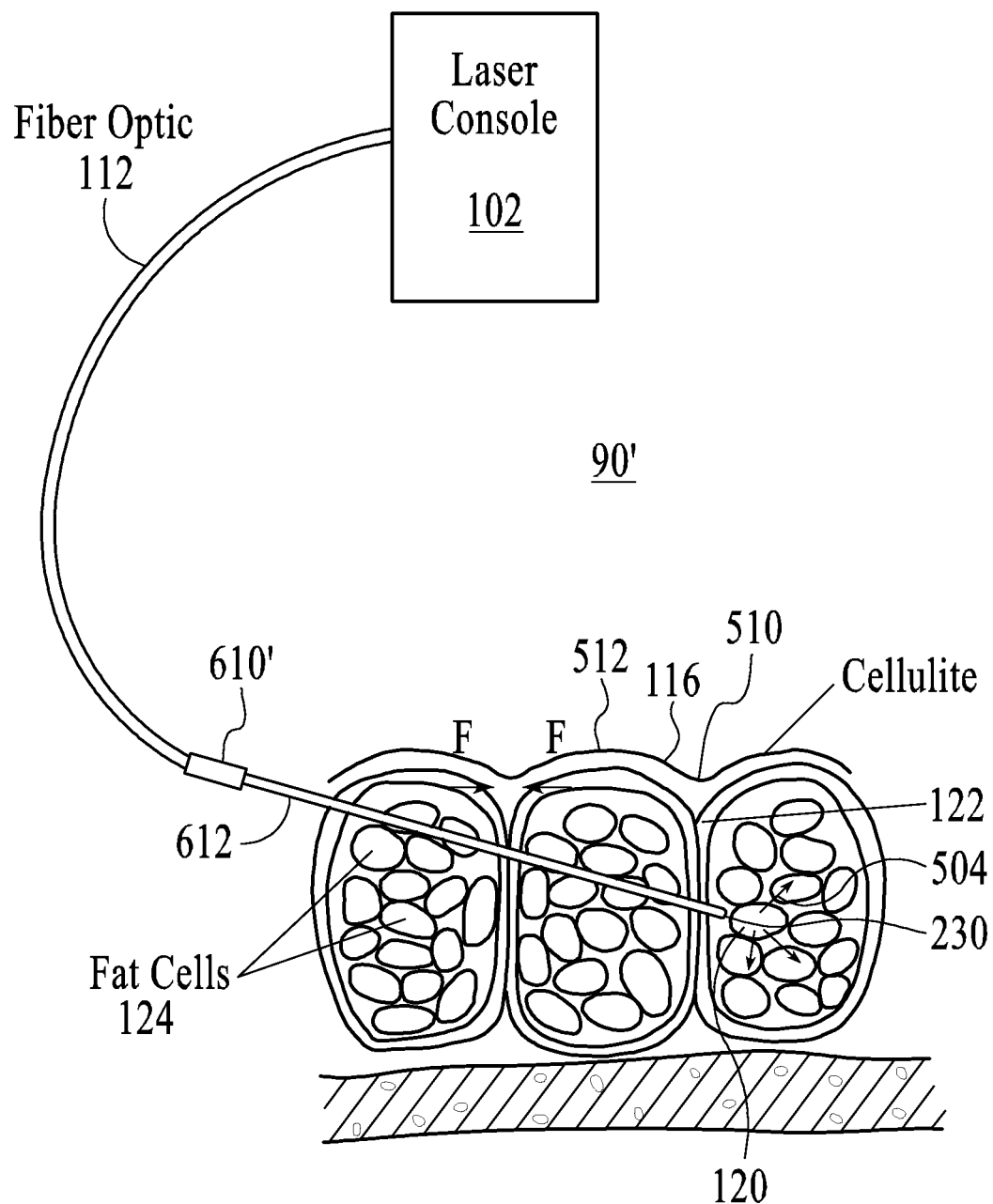
FIG. 4 is a representative detail schematic diagram of another embodiment of the cellulite and adipose tissue treatment system 90' of the present invention.

FIG. 4 is a representative detail schematic diagram of another embodiment of the cellulite and adipose tissue treatment system 90' of the present invention. The system 90' was originally disclosed in related U.S. application Ser. No. 11/675,028 by Hennings et. al., which is incorporated herein by reference in their entireties, and claims any and all benefits to which they are entitled therefrom. As shown, the laser energy from the energy source 102 is directed into delivery device 112 which may be a fiber optic, articulated arm, or an electrical cable etc. At the distal end of delivery device 112 is a front fire fiber optic probe 610' for directing the pulsed energy 504 inside the target tissue 120. The front fire fiber optic probe 610' is protected by a long sheath or cannula 612' for easy access. The optical fiber delivery device 612' has a forward-firing firing tip 230 for safe laser treatment, which may optionally comprise mechanical disruption or breaking of the collagen fibers 122 or other target tissue 120 when in contact therewith.

A principle of treatment system 90 and 90' of the present invention is to selectively shrink some of the connective tissue 122 while weakening and stretching others; all while neighboring fatty tissue 124 is avoided. As shown best in FIG. 3 and FIG. 4, multiple bursts of pulsed energy 504, which is ultimately from appropriate energy source 102 that compares and optionally matches the transmission bands of fatty tissue 124 and the absorption bands of collagen, are directed to target tissue 120. The pulsed energy 504 heats up connective tissue strands 122 in the valleys 510 of the cellulite and adipose tissue dimples to the temperature range of 70° C. plus so they are stretched and weakened. At the same time, connective tissue strands 122 comprising the hill top surface 512 of the cellulite and adipose tissue dimples are heated to the temperature range between 50° C. and 60° C. so they are shrunk to a certain degree. As a result, there is an inward pull in the direction indicated as F generated at the top of the dimples 512, collectively the appearance of cellulite and adipose tissue is eliminated and skin surface 116 is smoothed. The fatty tissue 124 may be heated enough to start to metabolize faster but the selective nature of laser energy 504 such as Nd:YAG at 1.32 µm will allow most of the energy to transmit directly through the fat tissue 124 to target the collagen containing connective fibrous strands 122. Also, the fat tissue 124 is needed to maintain a smooth and healthy appearance of the skin. As opposed to methods and systems of the prior art, fatty tissue 124 is spared during cellulite and adipose tissue treatment of the present invention.

Figure 5:
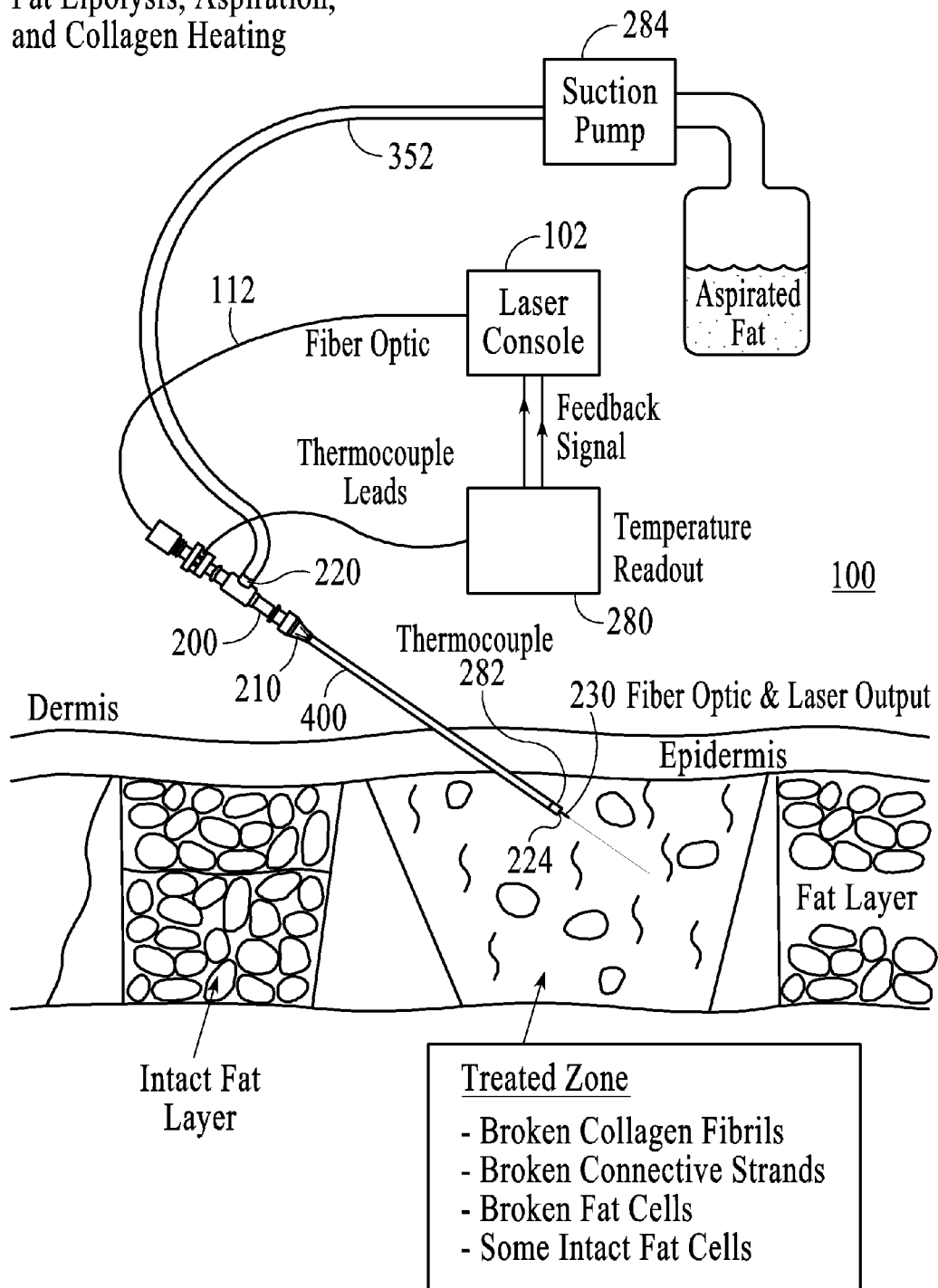
FIG. 5 is a representative schematic diagram of an embodiment of the thermally mediated tissue molding system 100 of the present invention.
Figure 7A:
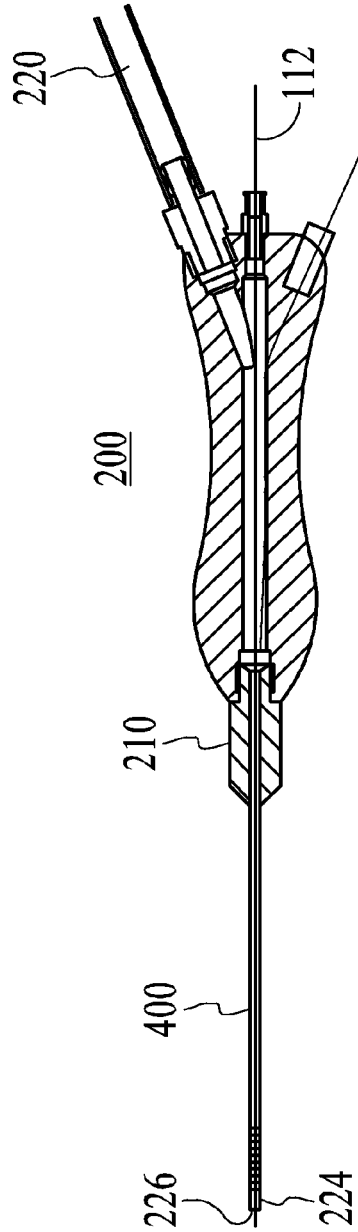
FIG. 7A is a representative cross-sectional view of an embodiment of the combined laser delivery handpiece 200 of the thermally mediated tissue molding system 100 of the present invention.
Figure 7B:
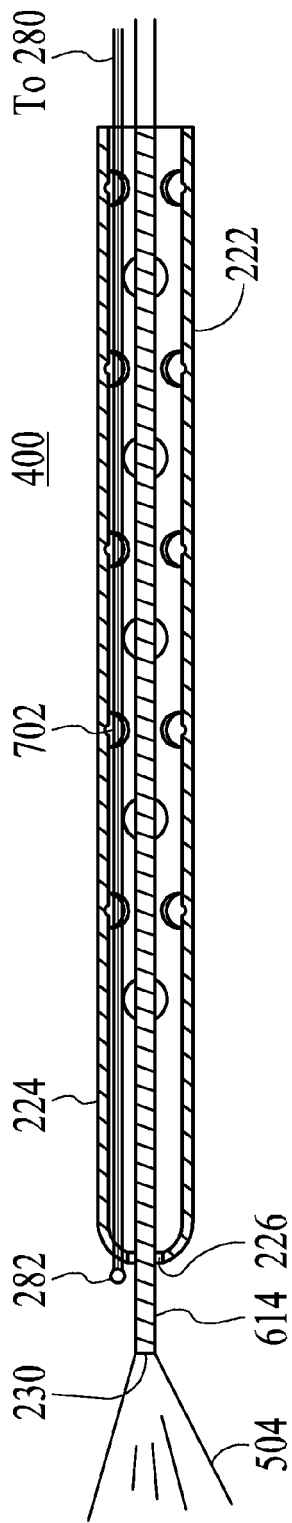
FIG. 7B is a representative cross-sectional view of an embodiment of hollow cannula 400 of the combined laser delivery handpiece 200 of the thermally mediated tissue molding system 100 of the present invention.

FIG. 5 is a representative schematic diagram of an embodiment of the thermally mediated tissue molding system 100 of the present invention. As shown in FIG. 5, based on the same principle of system 90 and 90', the thermally mediated tissue molding system of the present invention 100 is established to selectively shrink some of the connective tissue 122 while weakening and stretching others; all while neighboring fatty tissue 124 is avoided. As shown in FIG. 5, multiple bursts of pulsed energy 504, which is ultimately from appropriate energy source 102 that compares and optionally matches the transmission bands of fatty tissue 124 and the absorption bands of collagen, are directed to target tissue 120 via fiber optic 112 through combined laser delivery handpiece 200. In one embodiment, combined laser delivery handpiece 200 encapsulates the function of laser delivery, liposuction and thermal monitoring. An aspiration pump 284 connected to the combined laser delivery handpiece 200 at side port 220 can be used to remove excess fat and fluid in the subdermal cavity. A fiber optic 112 is used to deliver laser energy 504. A thermocouple 282 is used to detect subdermal tissue temperature near the probe tip 224 of hollow cannula 400 as best shown in FIGS. 7A and 7B. The pulsed energy 504 will ablate selective fat cells 124, heat and ablate connective tissue 122 and heat and denature fragments of collagen tissue in the lower dermis and subdermal treatment area, increase the temperature of subdermal tissue and eventually make the volume moldable.

The energy source 102 can be a laser that emits in the region of 1.3 μm-1.6 μm or it can be a. neodymium doped yttrium-aluminum-garnet (Nd:YAG) laser, energized by a flash-lamp or laser diode, at 1.32 μm, diode lasers at 1.45 μm, ER: Glass laser at 1.54 μm and fiber lasers at 1.55-1.60 μm. Energy source 102 is controlled by control system (NOT SHOWN) which comprises the software and electronics to monitor and control the laser system, and graphical user interface (NOT SHOWN). The beam of laser energy from the energy source 102 is directed into a delivery device which may be an optical fiber 112, a fiber bundle or articulated arm, etc. In the case of an Nd:YAG laser operated at a wavelength of 1.32 μm, it is extremely effective to selectively damage collagen containing connective tissue 122 in the presence of fat tissue 124. As best shown in FIGS. 1 to 5, fatty tissue 124 may be heated enough to start to metabolize faster but the selective nature of Nd:YAG laser at 1.32 μm will allow most of the energy to transmit directly through the fatty tissue 124 to target the fibrous strands of connective tissue 122. As best shown in FIG. 5, wherein system 100 of the present invention is used in a percutaneous manner utilizing combined laser delivery handpiece 200, wavelengths in the range of 800-2200 nm and 980-1700 nm would be very effective.

Collagen goes through several stages of alteration when heated. At temperatures lower than or around 50° C., collagen is not affected. At about 60° C., collagen may contract and shrink by about 30% without denaturization or permanent damage to the structure. It has been shown that at these temperatures the shrinkage is long term but the collagen remains viable. At temperatures greater than 65° C. however the collagen will denaturize and lose its elasticity and simply collapse. When this happens to a collagen containing connective fiber 122, the connective tissue 122 may weaken, stretch, and possibly break. Due to the nature of collagen, it is essential that the treatment system 100 of the present invention has a real time feedback and control on the temperature of subdermal tissue. As best shown in FIG. 5 and FIG. 7B, temperature of treated tissue 120 is detected by thermal sensory device 282 in real time. The other end of thermal sensory device 282 is connected to temperature feedback port 280 to provide temperature feedback which is ultimately looped back to the energy source control system. The purpose of the laser energy control is to heat up and maintain the subdermal tissue at the optimal temperature of approximately 60° C. where the tissue becomes pliable and moldable but not beyond repair.

Figure 8:
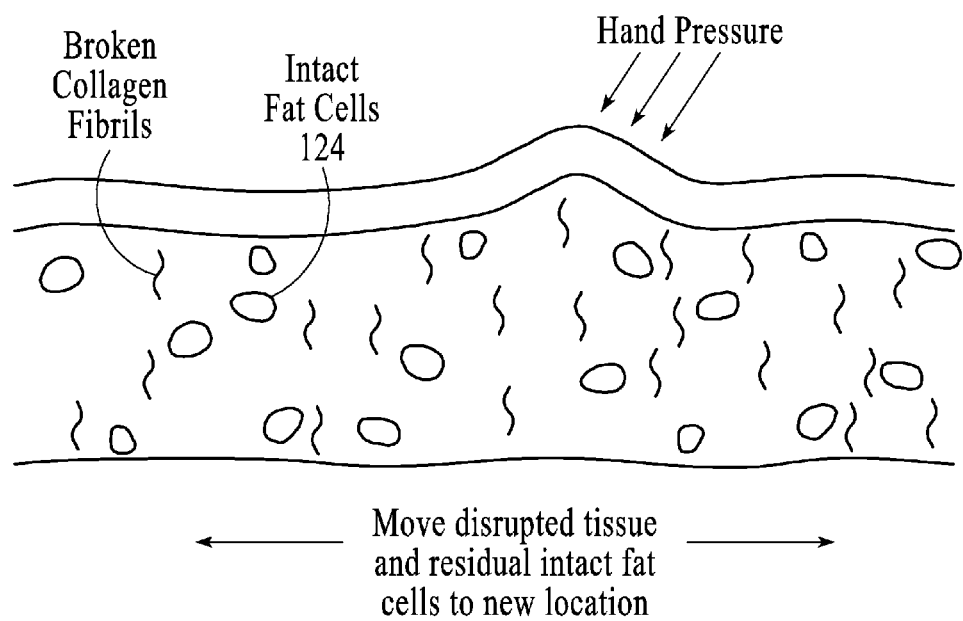
FIG. 8 is a representative schematic drawing showing the technique of molding and shaping the treated tissue 120.

As best shown in FIGS. 5 and 7B, liquefied fat tissue 124, blood and other tissues in the subdermal cavity are sucked through suction holes 702 (NOT SHOWN) of hollow cannula 400 and ultimately drained through the side port 220. Side port 220 is connected to suction pump 284, which provides the suction power, via aspiration tubing 352. This process combines liposuction or laser assisted lipolysis with skin shaping and facilitates the subsequent process of tissue molding as best shown in FIGS. 5, 8 and 9.

Figure 6:
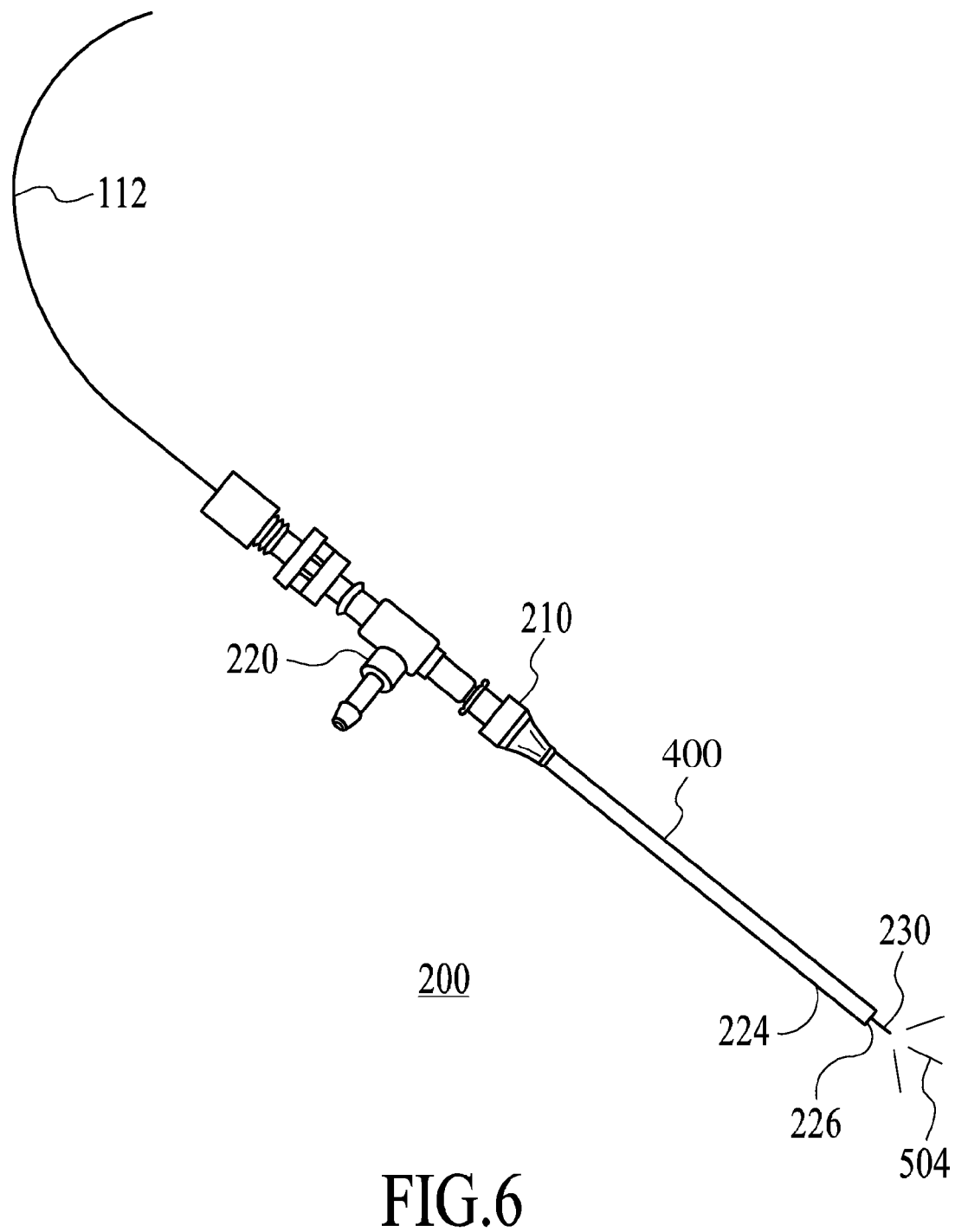
FIG. 6 is a representative isometric view of an embodiment of the combined laser delivery handpiece 200 of the thermally mediated tissue molding system 100 of the present invention.

FIG. 6 is a representative isometric view of an embodiment of the combined laser delivery handpiece 200 of the thermally mediated tissue molding system 100 of the present invention. As shown in FIG. 6, an embodiment of the combined laser delivery handpiece 200 comprises a fiber optic laser delivery device 112 which is secured into a Touhy Borst or equivalent clamp 210. A side-port 220 is useful for optional aspiration of liquefied fat, blood or other tissue. As shown, the Touhy Borst clamp adapter 210 is used to fix the length of the fiber 112 so that the fiber tip 230 of the optical fiber 112 is guaranteed to extend beyond the distal tip 224 of the hollow cannula 400. The Touhy Borst adapter 210 essentially clamps to the optical fiber 112 to mark proper extension of the fiber tip 230 past the distal end 224 of the hollow cannula 400. The hollow cannula 400 further comprises a tip bushing 226 at the distal end 224 which is made of protective, heat-resistant material including Teflon® and other suitable materials to prevent damage to the fiber tip 230 when fiber tip 230 is extending or protruding out. In one embodiment, fiber tip 230 assists in advancing the hollow cannula 400 by cutting through fibrous strands 122.

As described above, the present invention 100 is also a method for thermally mediated tissue molding by moving the distal tip 230 of the optical fiber 112 past the distal end 224 of the hollow cannula 400 so that heat does not impinge on the tip bushing 226 of the end of the hollow cannula 400 and heat it up. In one embodiment, the smooth and blunt end of the hollow cannula 400 prevents inadvertent puncture of skin and is safer overall to use. The apparatus includes a relatively stiff or rigid polyimide coated optical fiber 112, optionally cleaved flat or at an angle, providing the advantage of not requiring the use of the hollow cannula 400 and resistance by the fiber 112 to breakage particularly during placement or use. By extending the firing tip 230 of the fiber optic 112 past the distal end 224 and tip bushing 226 of the hollow cannula 400, the firing tip 230 is well beyond the distal tip 224 of the hollow cannula 400 and there is no risk of overheating the tip 224 or hollow cannula 400.

In one embodiment, the cladding of the fiber 112 is not stripped off prior to use. The fiber 112 can be cleaved through the entire coating. Thus, laser energy heats the coating creating a carbonized tip. Thus, the laser energy goes mostly into heating the fiber tip 230 and directly to target tissue 120. In one embodiment, the pulsed hot tip laser explodes the tissue and fat 120 without extensive thermal effects. Fat is liquefied or ablated, and the pulsed laser creates an explosively hot cutting tip 230.

In an embodiment, the fiber coating is made of a material which absorbs the laser energy at the wavelength utilized. During use, it is an advantage to cause the distal end of the coating to burn to a char during laser delivery. The char heats to a very high temperature and acts as a hot tip ablation device, having a hot, ablative cutting surface. In an embodiment of the present invention, the method using a pulsed laser in conjunction with a coated fiber 112 such that the rapid temperature rise at the charred fiber tip 230 causes an acoustic explosion which ablates and disrupts tissue. The pulsed energy ablates a zone of tissue with minimal peripheral or other unintended thermal damage. Photoacoustic ablation is similar to CW Nd:YAG sapphire crystal contact tip technology. The tip 230 requires an "initiation" to enable the carbon char at the distal end 230 of the coated fiber 112 to function as a hot cutting tip. The carbon layer on the tip 230 absorbs laser energy, creating an intense white hot ablation point. The system adds short pulse length pulsed energy to achieve a white hot acoustic ablation mechanism. Thus, ablation of connective tissue occurs at low energy fluences, with resultant minimal collateral damage.

The tip 230 of the coated fiber 112 can be inserted beyond or past the distal tip 224 of the hollow cannula 400 so that it is no longer adjacent the cannula tip 224, increasing maneuverability and improving the efficiency of the cutting tip 230. Additionally, by moving the distal tip 230 of the optical fiber 112 well past the tip bushing 226 of the hollow cannula 400 there is less chance that the metal cannula 222 will be heated by the laser beam exiting from the emitting face or tip 230 of the fiber 112, it provides an advantage to minimize heating of the tip 224 of the hollow cannula 400 which if heated may cause burns to the patient's skin as it is introduced and/or withdrawn before, during or after use.

It is also possible to use a Touhy Borst clamp 210 on the fiber 112 as a marker during other types of visualization including optical, X-ray, sonic imaging, MRI, CAT-scan or other spectral analysis visualization, to guarantee that the fiber 112 is well beyond the cannula tip 224. Using an aiming beam, up to 10 times or brighter than the conventional aiming beam, the practitioner can easily determine exactly where the fiber tip 230 is and be able to move it well past the cannula tip 224 before firing it to ablate undesirable connective tissue 122 and melt fat 120.

In one embodiment, the firing tip 230 of the fiber optic 112 extends beyond and projects out from a blunt distal end 224 of the hollow cannula 400 assisting in advancing the hollow cannula 400 by cutting through fibrous strands 122 as the firing tip 230 advances. The protrusion of firing tip 230 beyond the tip bushing 226 of the blunt distal end 224 of the hollow cannula 400 allows the simultaneous effect of fatty tissue 124 ablation and of heating fatty tissue 124 to cause collagen contraction or collagen stimulation which would not be possible with a fiber end enclosed within the end 224 of the hollow cannula 400.

FIG. 7A is a representative cross-sectional view of an embodiment of the combined laser delivery handpiece 200 of the thermally mediated tissue molding system 100 of the present invention.

FIG. 7B is a representative cross-sectional view of an embodiment of hollow cannula 400 of the combined laser delivery handpiece 200 of the thermally mediated tissue molding system 100 of the present invention. As best shown in FIG. 7B, there are a plurality of suction holes 702 on one or more sides of the hollow cannula 400 similar to conventional liposuction handpieces. The main function of suction holes 702 is to provide an opening to allow liquefied fat, blood and other tissues to drain during operation of the present invention 100. In one embodiment, fiber optic 112 protrudes out the distal end 224 of hollow cannula 400 by a sufficient distance to not be adjacent. Optionally, fiber optic 112 has a thin coating on it to prevent breakage. The hollow cannula 400 is used to aspirate or suction out tissue 122 or fat 124 that has been melted or ablated by the laser in the subdermal treatment area. The suction and aspiration occurs around fiber optic 112 inside the hollow cannula 400. As shown in FIGS. 6 and 7A, a Touhy Borst adapter 210 can be used to seal suction off from the suction port 220 on the hollow cannula 400. In one embodiment, fiber tip 230 will still exit the hollow cannula 400 at the distal end 224 near the tip bushing 226 which internal diameter is in close tolerance to the fiber tip 230 so that suction is not lost from the suction holes 702. In one embodiment, fiber optic 112 can be 100 to 1000 μm in diameter and preferably 320 to 600 um. The coating for fiber optic 112 can be Teflon® or other plastic. The coating is preferably a harder coating to allow additional room inside the hollow cannula 400 for aspiration. The hard coating on the fiber optic 112 is preferably polyimide but can also be gold or other hard materials. A thin coating is preferred to allow room inside the hollow cannula 400 for both the fiber optic 112 and the aspirated material to move without clogging up the hollow cannula 400.

The laser 504 can be any laser, either pulsed or continuos laser, that will ablate or melt tissue 122 or fat 124 and is transmittable through fiber optics 112. The laser 504 is preferably laser with wavelength of 800-2200 nm, 980-1700 nm or with a wavelength of 1320 nm if it is an ND:YAG laser. For pulsed laser, it is preferably laser with pulse length of 50-400 micro seconds. As best shown in FIGS. 5 to 7B, while fiber tip 230 is advancing, fatty tissue 124 is liquefied and causes increasing popping sound of the pulsed or continuous laser 504. The phenomenon will then trigger suction function of the hollow cannula 400. In one embodiment, liquefied fat tissue 124, blood and other tissues are sucked through suction holes 702, through the entire hollow cannula 400 and ultimately drained through the side port 220 and aspiration tubing 352. Aspiration and suction of liquefied fat, blood and other tissues in the subdermal tissue is only activated when the hollow cannula 400 is advancing and liquefied fat, blood and other tissues can be sucked out through the side port 220. In so doing, hollow cannula 400 is being pushed further into the liquefied fat and achieves the optimal and a higher laser ablation efficiency.

It is important that the treatment system 100 of present invention has a temperature sensor set up in a way that measures the temperature of the skin surface 116 in real time during the treatment pulse sequence and to control the energy source 102 and ultimately the intensity of laser power 504 with a feedback loop so that the skin temperature never reaches damage threshold. However, a non contact sensor can only detect skin surface temperature but not the dermal temperature. The disadvantage of this non contact method is that the measurement is not very accurate and largely depends on skin thickness, density and surrounding temperature. As best shown in FIG. 7B, there is a thermal sensory device 282 such as a thermocouple placed inside the hollow cannula 400. As best shown in FIG. 7B, thermal sensory device 282 is located behind the fiber tip 230 such that emitted laser power 504 does not impinge directly on the thermal sensory device 282 and artificially heat it up. In one embodiment, thermal sensory device 282 should only come into contact with treated tissue 120 after tissue has been heated up by the laser 504. Temperature of treated tissue 120 is then detected by thermal sensory device 282 in real time. The other end of thermal sensory device 282 is connected to temperature readout 280 to provide temperature feedback which is ultimately looped back to the energy source control system that control the intensity of laser console 102.

The treatment of the present invention does not depend upon optical absorption properties of fat. The pulsed hot tip laser energy explodes tissue and fat without extensive thermal effects. Fat is liquefied, not cooked. Thus, pulsed energy at 1320 nm wavelength ablates in a manner very similar to pulsed energy at 1064 nm. Furthermore, 1320 nm also tightens the sub dermal collagen better than energy at 1064 nm.

FIG. 8 is a representative schematic drawing showing the technique of molding and shaping the treated tissue 120. During the laser treatment as best shown in FIG. 5, the pulsed energy 504 ablates selective fat cells 124, heats and ablates connective tissue 122 and heats and denatures fragments of collagen tissue in the lower dermis and subdermal treatment area, increases the temperature of subdermal tissue to the optimal approximate range of 60° C. and eventually makes the volume pliable and moldable temporarily. Once the connective tissue 122 is broken or weakened the remaining intact fat cells 124 and collagen fragments can be moved to new sites in the subcutaneous space by gentle hand pressure or smoothing. When adequately treated with the laser the sub-dermal tissue feels and acts like warm clay and is highly moldable. The molded tissue will remain in place after molding.

Figure 9A:
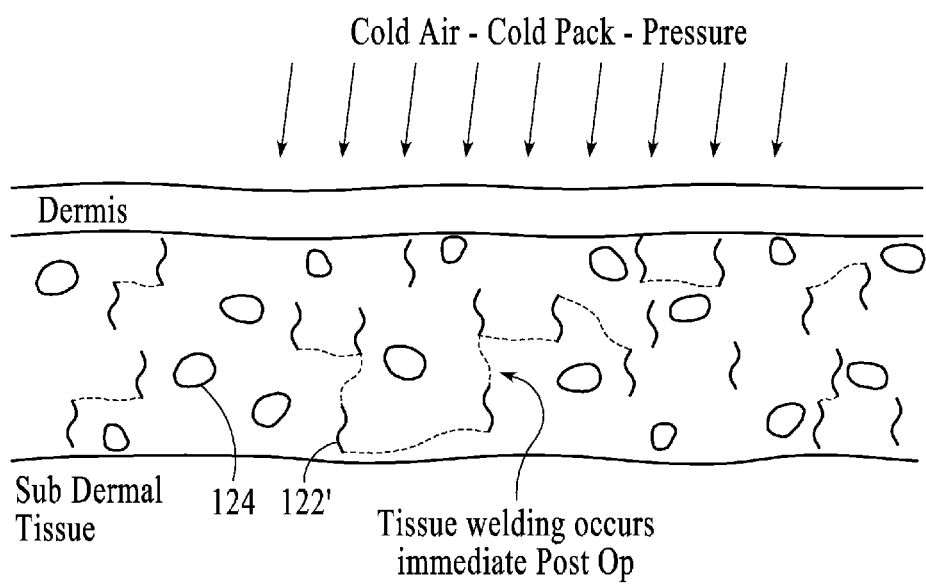
FIG. 9A is a representative schematic drawing showing how the new molded shape can be set and preserved.

FIG. 9A is a representative schematic drawing showing how the new molded shape can be set and preserved. After desirable shape and contour is achieved, the treated area will be exposed to cold air or cold packs while pressure is still asserted in the treatment area. The cold medium can be placed and directed on the skin to aid in the crosslinking of heated collagen fibrils in their new positions. The cooling process will also hold the residual intact fat cells 124 in their new positions. The skin can also be left to cool naturally.

Figure 9B:
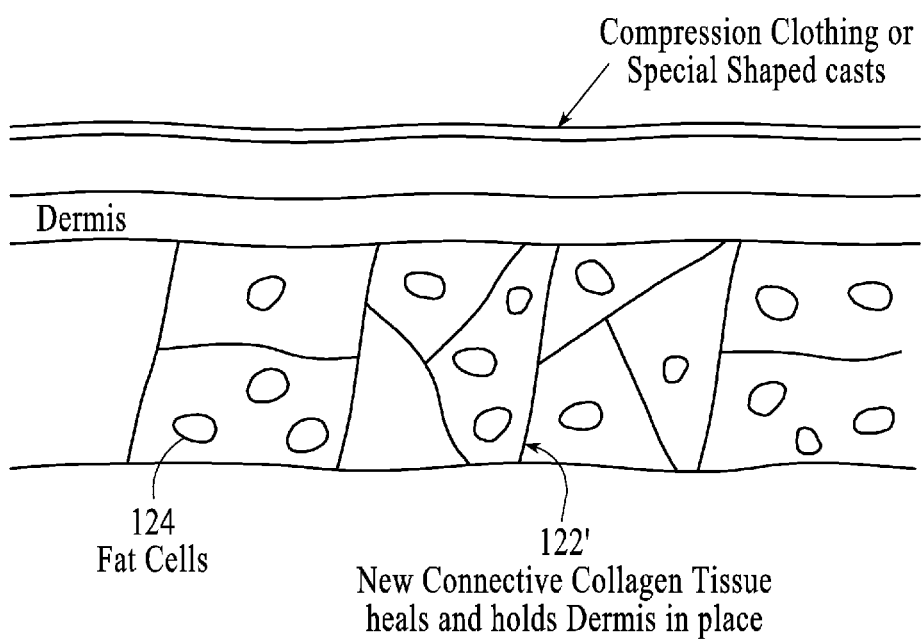
FIG. 9B is a representative schematic drawing showing the long term healing process that will hold the new skin shape.

FIG. 9B is a representative schematic drawing showing the long term healing process that will hold the new skin shape. It is advisable to wear compression clothing or special shaped casts post-surgery to help retain the new skin shape. The body's wound healing mechanism, which takes an approximate range of 2 to 12 months, will generate new collagen and connective tissue 122' in the treated and molded area.

Clinical Study

Key Words: Short Pulse, 1320 nm Laser, Neck and Lower Face Rhytidectomy—No Strings, No Scars Abstract/Objective:

A 100 usec pulsed 1320 nm laser (CoolLipo® by New Star Lasers, Inc.) was used on a number of different patients over a period of 15 months to develop a new method to selectively disrupt fat, i.e., photo-acoustic lipolysis causing little heat, and then tighten anterior neck, sub-mental, jowl and lower cheek skin via selective photo-thermallysis of the water in skin, for which reproducible end points have been determined. No excision or suspension of tissue is utilized, making this a preferred technique compared to the traditional gold standard of upper neck/lower face rhytidectomy.

Methods:

Over 30 cases were performed to refine the use of the 1320 nm laser with and without liposuction to define the most effective skin surface and tissue temperatures. Temperatures were measured with a MicroTherma 2T Thermometer and contact probe—www.thermoworks.com. Endpoints surface temp of 38 to 40 degrees Celsius were uniformly reached, warmed tissue became moldable and retained compressed shape. Contouring was achieved, and there were no visible or palpable skin burns or irregularities. Photo mechanical fat ablation is monitored and determined by increases/decreases in acoustic "popping", ease of moving laser fiber/cannula and achievement of desired body contour and size. Achieving the exact temperature range and holding it for several minutes was the key to tissue tightening by photo thermolytic effects.

Results:

Using the above endpoints and various hand pieces, all patients benefitted from this technique.

Conclusions:

The laser lipo neck lift is a safe, reproducible, effective treatment for ptotic anterior neck tissue, lower face fat and drooping, loose or lax skin for all ages and skin types. It compares favorably with traditional rhytidectomy, but also causes no surgical significant scars and has a much shorter recovery. It can be bundled with Botox, and other modalities etc.

The tissue molding effect is both immediate and can be effective up to 12 months post operation.

The immediate effect is due in part to tissue welding of heated collagen as it cools off. It is important to adequately sculpt and mold the skin while it is still warm and the collagen fibrils are not cross linked. Post operative cooling of the tissue with any known cooling means, including but not limited to cold air or cold packs, will help to set the tissue in a new shape.

The tissue is not completely shaped by the short term collagen cross linking however, and major additional strength comes as new collagen is formed in the molded and other affected tissue over the next 12 months. Patients have reported that their skin shows marks and grooves where elastic waist bands and other tight clothes have been up to 12 months post operation. This effect is far more pronounced than the normal marks created by some tight clothes and is evidence that the tissue remains still moldable until it is completely healed. Smooth compression garments and clothing or specially made rigid or semi-rigid casts can also be used for continuous molding, i.e., to continue molding the skin for 12 months post operation.

The present invention incorporates herein by reference in their entireties, without limitations, U.S. Pat. Nos. 5,820,626 issued Oct. 13, 1998 to Baumgardner and 5,976,123 issued Nov. 2, 1999 to Baumgardner et al., and in particular with regard to teachings regarding surface cooling of tissue during laser treatment.

U.S. Pat. No. 7,094,252 issued Aug. 22, 2006 entitled ENHANCED NONINVASIVE COLLAGEN REMODELING, U.S. Pat. No. 7,217,265 issued May 15, 2007 entitled TREATMENT OF CELLULITE WITH MID-INFRARED RADIATION, and U.S. patent application Ser. No. 11/612,324 filed Dec. 18, 2006 entitled ENDOVENOUS LASER TREATMENT GENERATING REDUCED BLOOD COAGULATION, are all incorporated herein by reference in their entireties, without limitation.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for tissue molding, the method comprising the steps of:
   providing a hollow cannula with a distal tip;
   providing an optical fiber laser delivery device with a distal emitting tip, the optical fiber laser delivery device capable of being inserted inside the cannula, the optical fiber laser delivery device extendable through the cannula, the emitting tip of the optical fiber laser delivery device extendable beyond the distal tip of the cannula, the proximal end of the optical fiber laser delivery device connected to a laser source;

providing a laser source with emitting characteristics for generating a laser beam transmittable through the optical fiber laser delivery device, the laser beam having an intensity and a wavelength capable of cutting connective strands in subdermal tissue;

generating a laser beam with the laser source and delivering laser energy from the distal emitting tip of the optical fiber laser delivery device;

placing the distal tip of the cannula underneath the skin of a patient;

placing the optical fiber laser delivery device into the hollow cannula;

moving the emitting tip of the optical fiber laser delivery device beyond the distal tip of the cannula into the subdermal tissue of the patient;

irradiating the subdermal tissue with the laser beam to disrupt the connective strands in the subdermal tissue; and molding the tissue into a desired configuration using compression to maintain the desired configuration until the tissue cools and retains its new shape.

2. The method of claim 1 in which the desired configuration is a flat configuration.

3. The method of claim 1 in which the distal tip of the hollow cannula further comprises an integral suction system.

4. The method of claim 1 in which the distal tip of the hollow cannula further comprises an integral temperature sensing and feedback system.

5. The method of claim 1 in which the step of molding the tissue is accomplished using a compression garment to maintain the desired configuration until the tissue cools and retains its new shape.

6. The method of claim 1 further comprising the step of irradiating cellulite and adipose tissue with the laser source to liquify the cellulite and adipose tissue.

7. The method of claim 1 further comprising the step of using suction to remove the liquified cellulite and adipose tissue.

8. The method of claim 1 further comprising the step of providing cooling to the surface of the tissue to prevent thermal damage to the surrounding skin and subdermal tissue.

* * * * *